United States Patent [19]

Weiner et al.

[11] 4,202,625
[45] May 13, 1980

[54] METHOD AND APPARATUS FOR DISCRIMINATING RED BLOOD CELLS FROM PLATELETS

[75] Inventors: Irving L. Weiner, Sharon; Russell J. Gershman, both of Middleboro, Mass.

[73] Assignee: Ortho Diagnostics, Inc., Raritan, N.J.

[21] Appl. No.: 934,938

[22] Filed: Aug. 18, 1978

[51] Int. Cl.² ...................... G01N 33/16; G01N 15/02
[52] U.S. Cl. ............................... 356/39; 250/222 PC; 324/71 CP; 356/336
[58] Field of Search ................. 356/39, 335, 336, 338; 250/222 PC; 324/71 CP

[56] References Cited

U.S. PATENT DOCUMENTS 4,110,604   8/1978   Haynes et al. .................... 324/71 CP

*Primary Examiner*—Vincent P. McGraw
*Attorney, Agent, or Firm*—Audley A. Ciamporcero, Jr.

[57] ABSTRACT

Signals including noise, platelet pulses, and red cell pulses are amplified and compared to a noise threshold. If larger than the threshold, the signals are integrated and the integrated signals are compared to respective red cell and platelet references.

7 Claims, 2 Drawing Figures

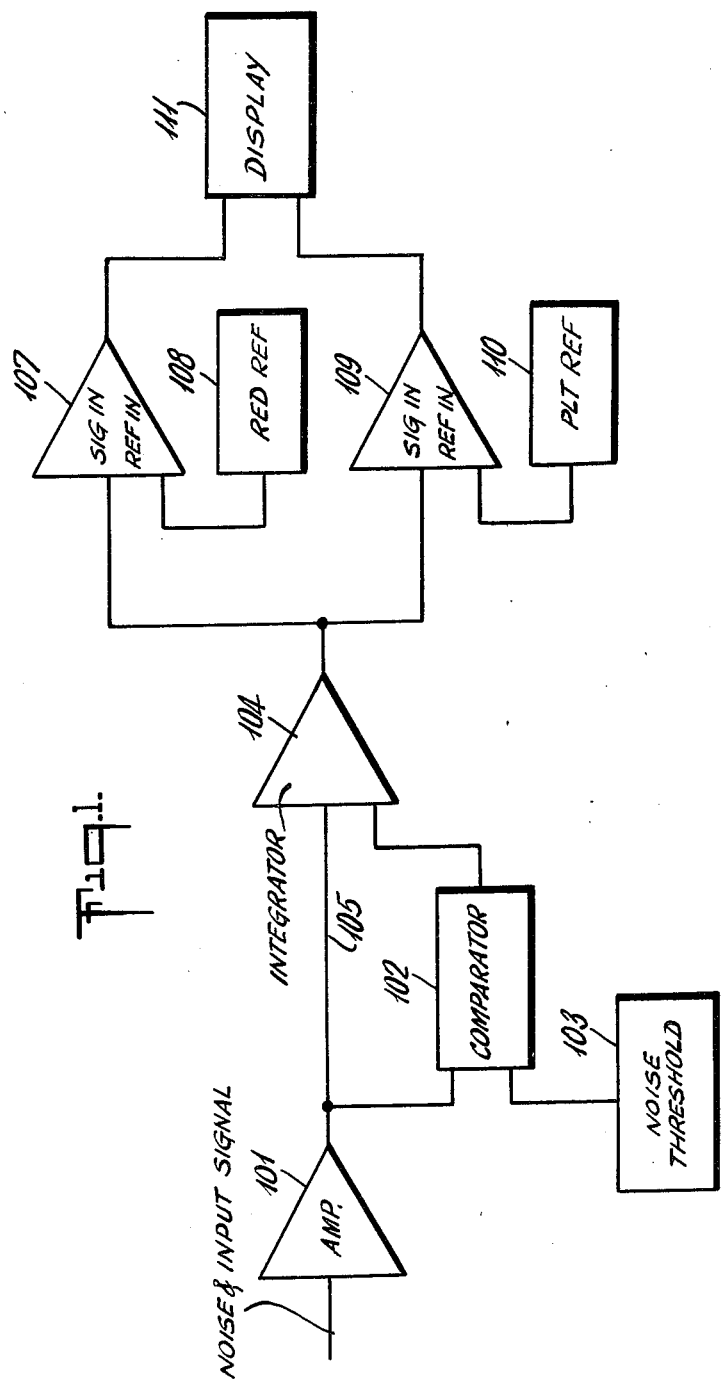

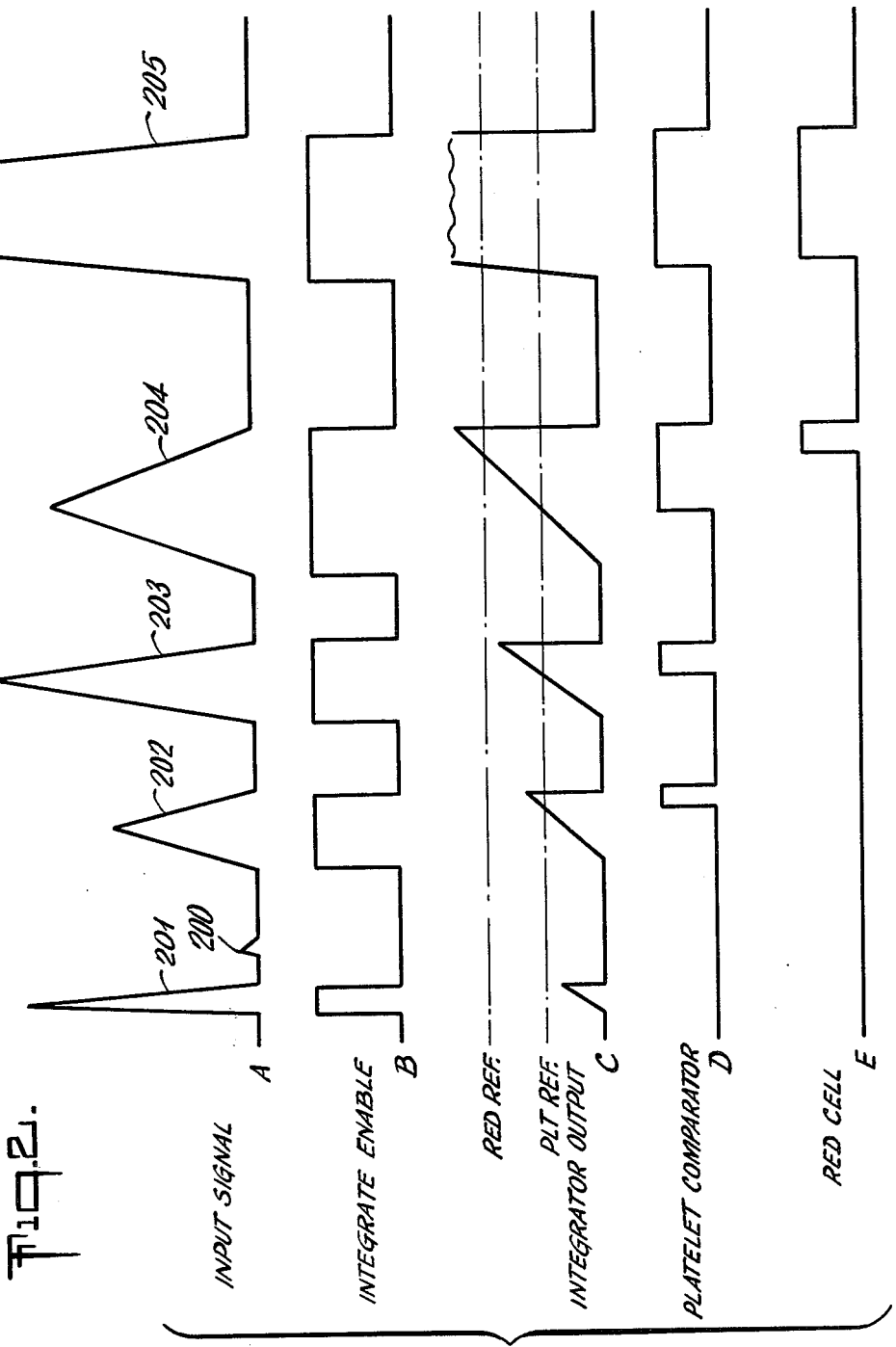

METHOD AND APPARATUS FOR DISCRIMINATING RED BLOOD CELLS FROM PLATELETS

FIELD OF THE INVENTION

This invention relates to methods and systems for blood analysis, and more particularly to methods and apparatus for discriminating platelets from red blood cells in blood analysis systems utilizing optical means to illuminate individual cells.

BACKGROUND AND PRIOR ART

One commonly known class of blood analysis equipment utilizes optical systems to irradiate and analyze individual blood cells. Typically, a small sample of blood is passed through a narrow fluid vortex, approximately one cell wide, a cell at a time at a very high rate. A source of light is focused onto the vortex, such that as cells pass through, they interact with the light beam, absorbing a portion and scattering the rest, depending upon the size, configuration, color, and the like of the cell. In some systems the light source is collimated and non-coherent, whereas in others, lasers are utilized. Further, some systems utilize direct light scattering measurements, whereas others employ the principle of the "dark field" microscope.

In any event, these systems employ an array of photoelectric means which generate a signal based upon the light scattered as the cells pass through the beam of light. Generally, the amplitude of the signal derived from scattered light tends to correlate reasonably well with the cells under analysis. For example, if the system is using the "dark field" concept, signal pulses corresponding to typical red cells are several orders of magnitude (e.g. six to ten times) larger in amplitude than those corresponding to typical platelets. Hence, for some applications, there exists an adequate basis for distinction between red cells and platelets simply based on the amplitude of scattered light.

For many other applications, however, it is beneficial, and sometimes essential, to distinguish red cells from platelets even more closely than upon amplitude discrimination. Thus, it may be useful to distinguish small red cells from large platelets, which would be relatively indistinguishable on a simple amplitude discrimination basis. Likewise, air bubbles, foreign particles, and the like should be recognized as such, and not be identified either as platelets or small red cells.

DISCLOSURE OF THE INVENTION

It is an object of the present invention to provide methods and apparatus for enhancing the ability of optical blood analysis instruments to distinguish red cells from platelets, and to distinguish both such types of cells from irregularities in the sampled blood, such as air bubbles or particulate matter.

The present invention is grounded on the proposition that red cells and platelets when respectively passed through a focused, collimated, or laser light beam at a given rate, will be relatively distinguishable from one another based not only on instantaneous light scatter, but furthermore based on the characteristics of scattered light during an interval of time. In other words, considering signals generated in response to measured light scatter, for example in systems utilizing the "dark field" concept, two-dimensional signal analysis (i.e. amplitude and time) will yield discrimination capabilities superior to a mere one-dimensional (amplitude) approach. An enhanced method of detection utilizes not only an amplitude discrimination with respect to a stationary noise level, but furthermore utilizes a subsequent signal integration, and analysis of the integrated signals, further to distinguish between red cells, platelets, and spurious indicators such as bubbles or particulate matter.

In an illustrative embodiment, cells are individually illuminated, and a signal is derived based on measured light scattered from the cells. These signals are suitably amplified and coupled simultaneously to an integrator and to a comparator, at the latter of which the signals are compared to a noise threshold. If they exceed the noise threshold, indicating likely presence of a cell to be analyzed, the integrator is enabled and the signal itself is integrated. The integrated signal is simultaneously coupled to first and second comparators, each of which is also provided with a comparison reference, on corresponding to platelets and another, larger one corresponding to red cells. If the integrated signal is smaller than both, it is deemed to be spurious; if it is larger than both, a red cell is deemed detected. In the interval between thresholds, a platelet is deemed detected.

DESCRIPTION OF THE DRAWINGS

FIG. 1 shows a block diagram schematic of a preferred embodiment of the principles of the present invention;

FIG. 2 parts A through E, show exemplary waveforms associated with the embodiment of FIG. 1, illustrating the processing of typical signals in accordance with the principles of the present invention.

BEST MODE FOR CARRYING OUT THE INVENTION

Although it will be apparent that the principles of the present invention apply to a variety of optical blood analysis systems, a preferred mode of application relates to systems of the type analagous to dark field microscopy. In such a system, whole blood is collected, mixed with anticoagulant, and diluted in an isotonic liquid medium. The dilute sample is pumped through a hydrodynamic focusing flow chamber, and a light source is brought to a focus upon the sample stream such that the light crosses at an approximate right angle to the axis of flow. The dimensions of the focal spot are made small enough to reduce cell counting coincidence to levels that are low enough to permit precise coincidence error corrections.

As each cell passes through the optical focal region, various fractions of the incident radiation are transmitted, scattered, and absorbed by the cell and the surrounding diluent. The transmitted radiation is then physically blocked by a contrived obstruction that matches the beam cross-sectional profile after exiting the flow chamber in the absence of cells. Scattered radiation passes around this contrived obstruction and is then collected by a lens or mirror. Absorbed radiation is presumably converted to other energy forms in the cell.

The collection optics for the scattered light is arranged so as to cast an image of the illuminated sample flow stream on an aperture, which is the same size as the illuminated flow stream image, and the collection optics' depth of focus is the size of the sample flow stream. Therefore, only scattered light that originates at the intersection of the incident focused radiation and the hydrodynamically focused sample stream is allowed to pass through the aperture. This radiation is sensed by a photodetector, which produces an electrical signal which may be processed and analyzed to yield information with respect to the cells causing the light scatter.

Referring to FIG. 1, which shows in block diagrammatic form an illustrative embodiment of the principles of the present invention, the signal, which for example has been generated in the method set forth above, is coupled to an amplifier 101. At this point the signal includes aspects corresponding to red cell signals, platelet signals, background noise, and noise signals such as may be generated by bubbles, spurious particulate matter, or the like. The signal from aplifier 101 is coupled to the input 105 of an integrator 104, and simultaneously to one input of a comparator 102. Normally, the integrator 104 is disabled, and the signal presented at input 105 is not integrated. At such time, the output of the integrator remains clamped at zero volts.

The second input of comparator 102 is coupled to a reference source 103, corresponding to a noise threshold. This noise threshold, which may be freely varied in accordance with the needs of the designer, may be conveniently set to eliminate a considerable amount of noise signals in the system; hence, the function of comparator 102 is essentially to identify signals from amplifier 101 which have sufficient amplitude to be candidates for identification as platelets or red cells. Whenever the signal from amplifier 101 rises above the noise threshold from source 103, comparator 102 energizes an enable terminal 106 to integrator 104, thereby energizing the integrator 104 to generate a running integral of the signal applied at input terminal 105. Correspondingly, whenever the signal from amplifier 101 falls below the noise threshold of source 103, comparator 102 disables the integrator 104 via the enable terminal 106 thereof, and the output of the integrator is once more clamped to zero volts.

The output signal from the integrator 104 is coupled simultaneously to respective inputs of comparators 107 and 109. It will be noted that comparator 109 is provided at its other input with a reference voltage from source 110, while comparator 107 is provided at its second input terminal with a reference voltage from source 108. In accordance with the principles of the present invention, reference source 110 provides a reference level corresponding to the identification of a platelet, and the reference level from source 108 provides a reference voltage corresponding to identification of a red cell. It will be appreciated that the precise levels of sources 108 and 110 will be a function of the voltage levels utilized throughout the system; in any event, the red cell reference from source 108 will produce a level larger than that produced by platelet reference source 110.

Signals from the integrator 104 which are smaller than the platelet reference from source 110 will not enable either comparator 107 or 109. Signals from integrator 104 which have an amplitude between the levels set by sources 110 and 108, will enable only the platelet indicating comparator 109. Signals larger in amplitude than the reference voltage produced by source 108 will enable both comparators 107 and 109. Hence, an enabling output signal from only the lowermost comparator 109 will indicate detection of a platelet, whereas enabling signals from both comparators 107 and 109 will indicate detection of a red cell. The output signals from comparators 107 and 109 are coupled to an appropriate display unit, thereby indicating the nature of the detected cell or cells. As is known in the art, the display unit 111 may include various signal processing circuitry for generation of histograms, scatter data, or the like.

The operation of the embodiment of FIG. 1 may perhaps be better appreciated upon consideration of the waveforms of FIG. 2. In particular, waveform A of FIG. 2 shows an exemplary waveform from the output of amplifier 101. It is to be understood that FIG. 2 part A may or may not be an actual waveform, but includes specific types of signals and pulses which might occur. "White" noise and the like is not depicted. Pulse 200 represents a spurious noise signal which might be generated anywhere in the optics or electronics of the system. Pulse 201 represents the sort of "noise" spike which might be generated from the likes of a bubble, spurious particulate matter, or the like, passing through the system. Pulse 202, on a relative scale with respect to the other pulses represents a typical platelet signal, whereas pulse 203 represents a large platelet. Pulse 204 represents a small red cell, whereas pulse 205, which is foreshortened for convenience, represents a typical red cell.

Waveform B of FIG. 2 shows the integrate enable signal at terminal 106; it will be noted that each pulse of the FIG. 2A waveform has triggered the integrator enable, with the exception of noise pulse 200, whose amplitude was insufficient to trigger comparator 102, inasmuch as it did not exceed the noise threshold 103.

Waveform C of FIG. 2 shows the output signal from integrator 104, with the platelet reference and red cell reference from sources 110 and 108, respectively, being as indicated. It will be noted that the integrated value of pulse 201 exceeds neither reference, whereas the integrated value of pulses 202 and 203 have peaks in the range between the platelet and red cell references. Accordingly, as is shown in waveform D of FIG. 2, the platelet comparator is thereby energized, but as shown in waveform E of FIG. 2, the output of the red cell comparator 107 is not energized. The display 111 would thereupon be energized to indicate detection of platelets.

As shown in part C of FIG. 2, the integrated values of pulses 204 and 205 exceed both reference thresholds, thereby enabling both the platelet comparator 109 (waveform D of FIG. 2), and the red cell comparator 107 (waveform E of FIG. 2). Under such a circumstance, the display 111 would indicate detection of red cells for each of pulses 204 and 205.

Although it will be apparent to those of ordinary skill that the various levels, integration rates, and the like are design parameters which may be varied freely, the following exemplary waveforms are provided for illustration:

Typical Platelet (Pulse 202) —300 mv; 0.5-2 $\mu$sec.
Typical Red Cell (Pulse 205)—3000 mv; 2-5 $\mu$sec.
Typical Noise (Pulse 200)—450 mv
Large Platelet (Pulse 203)—500 mv
Small Red Cell (Pulse 204)—400 mv
Noise Threshold (Source 103)—50-100 mv.
Platelet Reference (Source 110)—250 mv.
Red Cell Reference (Source 108)—2.5 v.

From the waveforms of FIG. 2, it will be seen that in accordance with the principles of the present invention, cell detection, discrimination, and identification is base upon two-dimensional signal analysis, as opposed to mere amplitude discrimination. Under such a circumstance, spurious signals such as noise spike 201 are eliminated from consideration. In strict amplitude systems, noise spike 201 would be interpreted as a cell, most likely as a platelet cell.

It will also be noted that the principles of the present invention account for discrimination of small red cells (pulse 204 of FIG. 2A), which in a strict amplitude system would be confused with signals relating to large platelets (pulse 203 of FIG. 2A). Thus, in a strict amplitude system, threshold levels would have to be set either to identify small red cells as platelets, or large platelets as red cells.

It will be understood that the foregoing set forth preferred and illustrative embodiments and features of the principles of the present invention, but that numerous alternative embodiments will occur to those of ordinary skill in the art without departure from the spirit or scope of the principles of the present invention.

What is claimed is:

1. A method of discriminating platelets from red blood cells comprising the steps of:
   passing the cells individually through a light field;
   measuring optical scatter produced by passage of cells through the field;
   generating a signal representative of said measuring;
   discriminating portions of said signal based on amplitude, thereby identifying possible signal representations of cells;
   further discriminating among said portions based on area of said portions, larger area portions being deemed red cells, and select smaller area portions being deemed platelets.

2. A method as described in claim 1 wherein said first discriminating step comprises comparing said signal amplitude with a predetermined threshold.

3. A method as described in claim 2 wherein said further discriminating step comprises integrating said signal, and comparing the integrated signal with successive thresholds respectively corresponding to platelets and red cells.

4. A method as described in claim 3 wherein said integrating step is enabled by detection, at said comparing step, of signals of at least said predetermined threshold.

5. In a blood analysis stem employing optical scattering measurements from illuminated individual cells, apparatus for discriminating platelets from background noise and red blood cells comprising:
   (a) means, responsive to optical scatter measurements, for generating a signal representative of said scatter;
   (b) an integrator;
   (c) means for coupling said signal to said integrator;
   (d) means for enabling said integrator whenever said signal is larger than a predetermined amplitude threshold; and
   (e) means for comparing the signal from said integrator with first and second thresholds respectively corresponding to platelets and red blood cells.

6. Apparatus as described in claim 5 wherein said means for enabling comprises:
   means for generating a reference threshold representative of specified types of noise; and
   means for comparing said reference threshold with said signal, and for enabling said integrator when said signal is larger.

7. Apparatus as described in claim 5 wherein said means for comparing comprises:
   means for generating first and second reference threshold levels, representative respectively of platelets and of red cells; and
   means for evaluating the integrated signal relative to said reference thresholds, signals larger than both being deemed representative of red cells, signals smaller than both being deemed spurious, and signals intermediate both being deemed representative of platelets.

* * * * *

UNITED STATES PATENT AND TRADEMARK OFFICE
CERTIFICATE OF CORRECTION

PATENT NO. : 4,202,625

DATED : May 13, 1980

INVENTOR(S) : Weiner et al.

It is certified that error appears in the above-identified patent and that said Letters Patent are hereby corrected as shown below:

Address of inventors on cover page "both of Middleboro, Mass" should read — Middleboro, both of Mass."

Column 2, line 19: "on" should be — one —.
Column 3, line 14: "aplifier" should be — amplifier —.
Column 4, line 64: "base" should be — based —.
Column 5, line 11: "set" should be — sets —.
Column 6, line 5: "stem" should be — system —.

Signed and Sealed this

Sixth Day of October 19

[SEAL]

Attest:

GERALD J. MOSSINGHOFF

Attesting Officer       Commissioner of Patents and Trademarks